Aug. 9, 1949. T. J. MORRIS Plant Pat. 861
ROSE PLANT
Filed Sept. 29, 1947
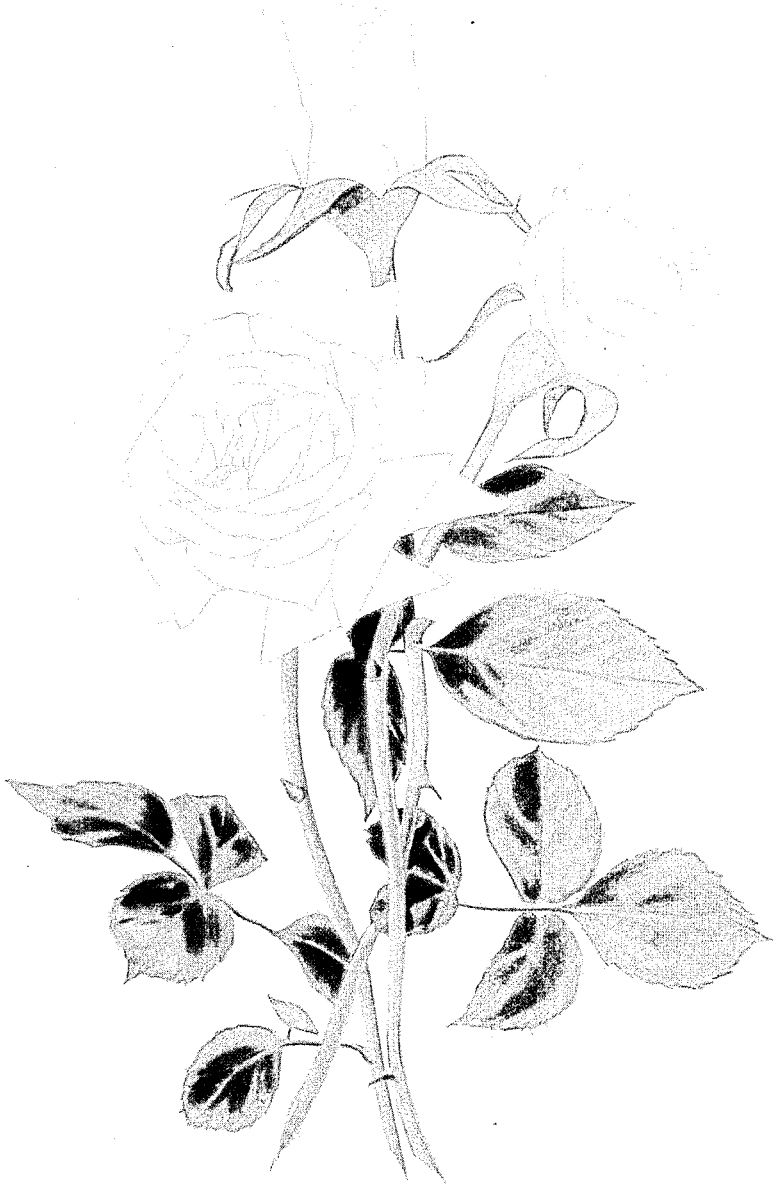
INVENTOR
Theodore J. Morris, dec'd.
by Lillian Adele Morris
Administratrix
By Orville M. Kile
Plant Pat. Agt.

Patented Aug. 9, 1949

Plant Pat. 861

UNITED STATES PATENT OFFICE

861

ROSE PLANT

Theodore J. Morris, deceased, late of Van Nuys, Calif., by Lillian Adele Morris, administratrix, Van Nuys, Calif., assignor to Germain Seed and Plant Company, Los Angeles, Calif.

Application September 29, 1947, Serial No. 776,779

1 Claim. (Cl. 47—61)

The present invention relates to definite improvements in hybrid tea rose plants, particularly those of the type producing flowers of yellow color. The variety was produced by hand pollination at greenhouses in Van Nuys, California, and it is the result of a cross between Lady Forteviot as the seed parent and Pedrables as the pollen parent.

The outstanding features of this new variety lie in its disease resistance and free production of velvety yellow blooms of good form. The variety has been asexually reproduced for several years and its distinguishing characteristics appear to be permanent.

Accompanying illustrations show in approximately their true colors, three specimens of the flowers of this new variety in various stages of opening, together with portions of their stems and foliage.

Following is a detailed description of the new variety of rose plant. Color plate references are to Horticultural Colour Chart issued by the British Colour Council.

*The plant*

Form: Bush; branching.
Growth habit: Medium in size but vigorous.
Disease resistance: Particularly resistant to mildew and black spot.
Blooming habit: Recurrent and very profuse.
Foliage:
- *Number of leaflets.*—Five.
- *Size.*—Medium.
- *Quantity.*—Normal.
- *Color of new foliage.*—Upper side bronzy, under side purplish.
- *Color of old foliage.*—Upper side grey green, under side normal leaf green.
- *Shape.*—Oval pointed. Edge cut with single, large, sharp serrations.
- *Aspect.*—Upper side glossy, under side rough. Ribs and veining light.
- *Texture.*—Substantial.
- *Leaf stem or rachis.*—Upper side grooved and green; under side has prickles.
- *Stipules.*—Long and ciliate.

Wood:
- *Aspect.*—Smooth bark, with many thorns.
- *Color.*—New wood gray green, old wood green.
- *Thorns.* — Quantity ordinary. Irregularly spaced, reddish-brown, medium length, wide base, and downward-hooked.

*The flower*

Bud:
- *Size.*—Medium.

- *Form.*—Long pointed. Later somewhat cylindrical.
- *Opening.*—Bud opens well. Not affected by hot or wet weather.
- *Color.*—When they first divide, Lemon Yellow (Plate 4); when beginning to unfurl, Aureolin (Plate 3/2); when half blown, inside Lemon Yellow (Plate 4) shaded to Buttercup Yellow (Plate 5/2) and outside Buttercup Yellow (Plate 5/2) shaded to Lemon Yellow (Plate 4/2). Edges of outer petals fade slightly in hot sun.
- *Sepals.*—Smooth, mostly simple but slightly branched. Curl backward in latter part of tight bud stage. Calyx is pear-shaped, medium-broad and smooth. When rubbed it has a Sweet Briar odor.

Bloom:
- *Size.*—Medium; average size when fully expanded, about 4½ inches.
- *Borne.*—Singly on long stems.
- *Form.*—Cup shaped, with outer petals reflexing and petaloids irregularly arranged in centre.
- *Petalage.*—Double; about 40 petals under normal conditions.
- *Color.*—Center of flower, Buttercup Yellow (Plate 5/1). Outer petals, Lemon Yellow (Plate 4/1) on outside of petals and Lemon Yelow (Plate 4/2) on inside of petals. Veinings and base slightly darker yellow.
- *Discoloration.*—First day, Lemon Yellow (Plate 4/1); second day, Aureolin (Plate 3/2); third day, Dresden Yellow (Plate 64/3).
- *Lastingness.*—Flowers last well as cut flowers.
- *Fragrance.*—Strong; Sweet Briar.

Petals:
- *Texture.*—Thick and soft. Not affected by hot weather.
- *Appearance.*—Inside and outside both velvety.
- *Form.*—Oval.
- *Arrangement.*—Irregular. Petaloids in the flower are few and large, and are particularly irregular in their arrangement.
- *Persistence.*—Petals hang on until dry.

Genital organs:
- *Pistils.*—Many, bunched. Styles columnar, medium and even in length, and very thin. Stigmas red.
- *Stamens.*—Filaments long and yellow. Arranged regularly around styles and mixed with petaloids. Anthers yellow and medium in size.
- *Pollen.*—Golden yellow.
- *Ovaries.*—Some protruding from calyx.

Fruit: Variety is sterile with own pollen. Russet Brown, smooth and flat headed. Sepals permanent and recurved.

Having thus disclosed this invention, I claim for the inventor:

The new and distinct variety of hybrid tea rose plant, substantially as herein disclosed, characterized particularly by its disease resistance, its very free blooming habit, and its medium-sized flowers having a strong Sweet Briar fragrance, deep yellow color with veinings of petals a deeper yellow, and the novel form including quilled outer petals and irregular arrangement of the petaloids.

LILLIAN ADELE MORRIS,
*Administratrix of the Estate of Theodore J. Morris, Deceased.*

No references cited.